United States Patent [19]

Binder et al.

[11] Patent Number: 5,426,428

[45] Date of Patent: Jun. 20, 1995

[54] MEASURING ARRANGEMENT

[75] Inventors: Hans Binder, Vienna; Gerd Lohninger, Ternitz, both of Austria

[73] Assignee: SBM Schoeller-Bleckmann Medizintechnik Gesellschaft m.b.H., Austria

[21] Appl. No.: 32,010

[22] Filed: Mar. 16, 1993

[30] Foreign Application Priority Data

Dec. 15, 1992 [AT] Austria ................... 2481/92

[51] Int. Cl.⁶ .................... G01K 1/14; G01K 13/08
[52] U.S. Cl. .................... 340/870.17; 374/208; 340/870.01
[58] Field of Search ........... 340/870.17, 870.1, 870.21, 340/870.11; 374/100, 208–210, 104; 324/696; 73/304 R, 292, 866.5; 341/155

[56] References Cited

U.S. PATENT DOCUMENTS

| 3,880,007 | 4/1975 | Emschermann et al. ............ 374/104 |
| 4,059,764 | 11/1977 | Belasco et al. ...................... 750/352 |
| 4,109,527 | 8/1978 | Goode, Jr. .......................... 73/343.5 |
| 4,541,730 | 9/1985 | Comey et al. ....................... 374/43 |
| 4,587,492 | 5/1987 | Laudermilch ....................... 324/318 |
| 4,800,513 | 1/1989 | Deutsch . | |
| 5,257,863 | 11/1993 | Chu et al. ......................... 340/870.17 |

FOREIGN PATENT DOCUMENTS

| 388502 | 7/1989 | Austria ............................ A61L 2/06 |
| 0168518 | 1/1986 | European Pat. Off. . | |
| 0075620 | 8/1986 | European Pat. Off. ...... G08C 19/00 |
| 2219405 | 9/1974 | France . | |
| 2308887 | 9/1974 | Germany ......................... G01K 1/12 |
| 2428890 | 1/1976 | Germany ......................... G01K 13/08 |
| 2509787 | 9/1976 | Germany ......................... G12B 17/06 |
| 2720118 | 11/1978 | Germany ......................... G12B 17/06 |
| 2852679 | 6/1980 | Germany ......................... G01K 13/08 |
| 3545215 | 11/1986 | Germany ......................... F27B 9/40 |
| 1152833 | 5/1969 | United Kingdom . | |
| 2151030 | 7/1985 | United Kingdom . | |

Primary Examiner—James J. Groody
Assistant Examiner—Glenton B. Burgess
Attorney, Agent, or Firm—Rothwell, Figg, Ernst & Kurz

[57] ABSTRACT

A measuring arrangement for autoclaves or similar arrangements under heavy climatic conditions includes at least one measuring probe, a measuring electronics connected with the measuring probe via a connection line and arranged in a thermally insulated container. The measuring electronics includes a transmitter unit to which a transmitting antenna is associated, which is arranged outside of the container on a lid provided therefor and is connected via a connection line. A separate receiver unit is associated with a receiving antenna. The thermally insulated container contains two oppositely oriented Dewar vessels arranged one within the other, the inner Dewar vessel accommodating the measuring electronics. The connection lines are led through the interspace between the Dewar vessels and are connected to a coupling tightly provided in the lid. A corresponding coupling is associated with the coupling means for connecting the transmitting antenna and the connection line to the at least one measuring probe. The measuring electronics includes an analog/digital converter for digitalizing the measured data as well as a digital control and processor module followed by the transmission unit.

17 Claims, 10 Drawing Sheets

MEASURING ARRANGEMENT

BACKGROUND OF THE INVENTION

The invention relates to a measuring arrangement for autoclaves or similar devices under heavy climatic conditions, comprising at least one measuring probe for detecting physical quantities to be measured, e.g., a temperature measuring probe, a measuring electronics connected or adapted to be connected with the measuring probe via a connection line and arranged in a thermally insulated container, which measuring electronics includes a transmitter unit to which a transmitting antenna is associated, which is arranged outside of the container on a lid provided therefor and is connected or adapted to be connected via a connection line, and a separate receiver unit to which a receiving antenna is associated.

In measuring technology, there are often situations where given measuring quantities, such as temperature, pressure, etc., are to be detected under difficult or critical conditions, such as, for instance, under vapor atmosphere, in hot-water sterilizing apparatus, or, in general, at elevated temperatures, elevated pressures and the like. Typical example are vapor sterilizers or sterilizing autoclaves, as they are used, for instance, in the food industry or in the pharmaceutical industry in order to sterilize food, infusions, solutions and the like products by means of water vapor at an elevated temperature and an elevated pressure. Primarily in the pharmaceutical industry, highly precise temperature measurements on several sites within the autoclave are required for the validation and process control of the sterilizing process. With stationary autoclaves, temperature probes usually are introduced into the autoclaves via leadthroughs. However, with rotating autoclaves, such a technique is not applicable. Thus, with conventional apparatus for rotating autoclaves the measured values are stored during the sterilizing treatment, the apparatus being ready for inquiry on the progression of sterilization only after completion of sterilization and unable to transmit measured values during the treatment process, for instance, in order to enable prompt reaction on changing sterilization conditions.

Such measured value storing in an electronic storage device within a temperature-insulated container is described in DE-C-23 08 887, for instance, in connection with the sterilization of tins, with a measuring electronics largely free of errors being sought, in particular. Such storing of measured values, such as temperature values, during a treatment procedure might be acceptable in the sterilization of tins, because there the sterilization treatment is not that crucial and repetition of the sterilization treatment is necessary only rarely, if required on grounds of the subsequent evaluation of the measured values stored. This is completely different with the abovementioned pharmaceutical products, with which a sterilizing temperature must be observerd over a defined period of time with great accuracy in order to safeguard sterilization to the desired extent. If, in that case, a deviation of the sterilizing temperature during a defined period of time, based on the measured values stored, is detected only afterwards, the sterilizing procedure must be repeated for these products, which, in practice, involves high expenditures in terms of time and money on account of several treatment repetitions. Therefore, in practice, a comparatively long sterilization time is provided from the very beginning for reasons of safety, treatment repetitions, thus, proving necessary only rarely; however, this involves the disadvantage of a comparatively long sterilization time being generally required.

On the other hand, the problem of an adequate thermal insulation in case of such sealed measured-value storing containers can be solved more readily than in those cases where the external transmission of measured values is constantly required. This is due not only to the fact that the connections to the measuring probes are to be made tight, but also that it is easier to keep the electronics in a thermally insulated container, thus also requiring comparatively little space. Hence it is possible to accommodate the measuring electronics plus storage and battery within the container having given external dimensions even with a highly complex insulation. If, however, the circuitry has to be extended for the transmission of the measured values, this involves a larger space demand within the container, the thermal insulation thus having to be designed less complex at given external dimensions of the container. On the other hand, enlargement of the container is not possible in most cases, because the space provided for such containers in autoclave charging cars usually is very limited. Apart from this, there will be an increased demand for insulation going hand in hand with an increased external surface on grounds of the thus increased heat transfer surface, a noticeable gain of space being feasible only with relatively extensive container dimensions.

Special temperature protection vessels for measuring means, furthermore, can be taken from DE-C-25 09 787 as well as from DE-A-27 20 118, which, however, are very complex in construction on account of incorporated water reservoirs. Moreover, a temperature protection vessel for a battery operated measured value circuit memory is described in DE-C-35 45 215, wherein it is considered advantageous that, due to the storage of the measured values in the electronic memory circuit, the otherwise necessary trailing cable connection to a display station and a high-frequency signal transmission from the furnace during the furnace campaign of the open-ended furnace car can be obviated. As pointed out, such measured value storage results in a simplified structure and circuitry, yet it involves the disadvantages of frequently repeated heat treatments in case of critical products, in particular, sterilization treatments in case of pharmaceutical products.

In connection with vapor sterilizers, measured data transmission from the sterilizer by radiotelegraphy was generally proposed in AT-B-388 502. As a temperature protection container, a metallic double-shell container is proposed, the cavity between the shells having to be evacuated and filled with celite. The measuring electronics is cast into paraffin together with the transmitter circuit in the interior of this container and is connected with the individual measuring probes via electrically insulating leadthroughs provided in the lid of the metallic container. In fact, this known measuring arrangement has never been successful in practice, and experiments carried out with similar measuring arrangements, which have led to the present invention, have proved that only insufficient functioning can be attained with measuring arrangements of this kind. In detail, an inadequate thermal insulation of the measuring electronics within the metallic container and hence errors in the measured value transmission result in addition to the fact that also the conduit leadthrough in the lid of the container cannot be made sufficiently tight and is cumbersome in handling. In total, only extremely short operation times are obtained with the known measuring arrangement, i.e., the known measuring arrangement each can be employed only for a rather short sterilization procedure. After this, the container must be replaced with a new one, because too high an internal temperature has already prevailed in the previously used container. In addition, the circuit calls for recharging of the used batteries after a relatively short time. In practice, these disadvantages apparently have led to the sustained use of measuring arrangements based on measured value storage as discussed above in vapor sterilizers.

Furthermore, it is also known, for monitoring the temperature of rotating machine parts, such as, for instance, heating rolls or rotors of electric equipment, to transmit the temperature data to a stationary means in a wireless manner. To this end, light-emitting diodes (LEDs) in connection with modulated light radiation may be used, cf. e.g., EP-B-75 620 and DE-A28 52 679, or capacitive transmission by means of a capacitor, one plate of which co-rotates with the rotating part of the machine and whose counter-plate is stationarily arranged, cf. e.g., DE-C-24 28 890. However, such transmission means for the wireless transmission of measured values obviously are not or not readily applicable to vapor sterilizers or autoclaves, primarily because the light transmission by aid of LEDs would, for instance, be impeded by the vapor present and the LEDs could hardly be thermally insulated to a sufficient extent at such elevated temperatures. Similarly, the capacitive transmission would be falsified by the vapor present between the capacitor plates.

SUMMARY OF THE INVENTION

It is, therefore, an object of the invention to provide a measuring arrangement as indicated above, which enables wireless measured-value transmission without errors over long cycle times such that reliable and economical measurements, e.g., of the temperatures prevailing even in rotating autoclaves, are feasible. In this connection, as little structural expenditures as possible are sought, and on-line interventions are to be rendered feasible in a process monitored by this measuring arrangement, e.g., in a sterilizing process, by continuous precise measurement and evaluation of the measured results without falsification by temperature influences or the like.

To achieve this object, in the measuring arrangement of the initially defined kind, the thermally insulated container contains two oppositely oriented Dewar vessels arranged one within the other, the inner Dewar vessel accommodating the measuring electronics; the connection lines are led through the interspace between the Dewar vessels and are connected to coupling elements tightly provided in the lid, to which corresponding coupling elements are associated for connecting the transmitting antenna and the connection line to the at least one measuring probe; the measuring electronics comprises an analog/digital converter for digitalizing the measured data as well as a digital control and processor module followed by the transmitter unit.

With the present measuring arrangement, a functionally safe wireless measured-value transmission of analogous measuring quantities, such as pressure, temperature, etc., is possible both in rotating and in static autoclaves or the like over extended periods of time or cycle times, wherein the thermally insulated container (the so-called "measuring bottle"), which is placed in the autoclave, offers both a good thermal insulation and also sufficient space for the electronic component contained therein as well as for rechargeable batteries (accumulators) provided for the power supply.

More specifically, it is of substantial importance that the two Dewar vessels arranged one within the other in a relatively close manner, for instance, at a distance of about 0.5 mm, enable the sufficient thermal insulation sought, wherein surprisingly not even the wiring means arranged in the interspace between the Dewar vessels affect the insulating effect, extensive heating of the measuring electronics in the interior of the Dewar vessels, thus, being safely avoided. In fact, there is a relatively long path for a possible heat transfer in the interspace between the two Dewar vessels arranged one within the other, which path corresponds to the path of the connection lines between the measuring electronics and the coupling elements on the lid. This long path surprisingly will do to prevent the formation of adverse thermal bridges from the surroundings to the measuring electronics. The coupling elements provided in the lid are important to the desired insulation as well as to the assemblage of the container containing the Dewar vessels arranged one within the other, not only ensuring the desired tight closure without any problem as in contrast to simple cable passages, but also facilitating (pre-)mounting of the measuring bottle together with the incorporated measuring electronics. On account of the reduced space offered by the Dewar vessels arranged one within the other at given external dimensions of the measuring bottle, thus calling for the use of relatively small rechargeable batteries or accumulators, the measuring electronics must be adapted with a view to a low power consumption in order to reach acceptable cycle times. This is ensured by the measured data digitalization and the digital circuit components to be used therefor.

As a result, a high measuring accuracy is attained also at high autoclave temperatures, enabling the continuous monitoring of the measured quantities, in particular, of the temperature. With sterilization treatments for the pharmaceutical industry, there is also the possibility of, for instance, determining the so-called FO-value (the FO-value being a common parameter for a certain extent of sterilization) and, hence, the optimization of the sterilizing process in on-line technique, wherein it is possible to stop the sterilization process as soon as a predetermined FO-value has been attained, thus saving time, energy and costs.

In order to be able to switch on the measuring electronics always only immediately before its use in the autoclave conveniently and to switch off the same immediately upon its use so as to save energy as well as to be able to simply recharge the battery, a further coupling element may be attached to the lid of the thermally insulated container and may be connected to a rechargeable battery and to the power supply terminals of the measuring electronics. Thus, similar tight couplings are provided in the lid of the thermally insulated container for all of the terminals, i.e., for those leading to the measuring probes as well as for the transmitting antenna and also for the battery recharging means and for the on/off circuit. These electric couplings, in principal, may, for instance, be screwed pipes, yet the coupling elements advantageously are plug connection elements. The coupling elements or plug connection elements, which are attached to the lid, can be mounted in a relatively simple manner, e.g., by O-rings or the like, so as to be tight and heat-insulating. When using the thermally insulated container including the measuring electronics, the components to be connected externally, i.e., the measuring probe and the transmitting antenna, may simply be plugged in or screwed in.

For a particularly good thermal insulation, it has proved suitable if the two Dewar vessels are embedded in an insulating layer of aluminum oxide ceramics.

With a view to the digitalization of the measured data in the measuring electronics contained in the thermally insulated container, and the thus involved energy-saving configuration of the digital circuit, it is also possible to additionally use the processor and control module for other functions without an increased power consumption. Accordingly it is of a particular advantage if the processor and control module ($\mu$C) comprises a coder for coding the digitalized measured data, e.g., a Hamming coder. In this manner, error correction may additionally be provided in measured data detection and transmission without calling for additional means. In detail, it is, for instance, possible to correct 1-bit errors and to detect multiple-bit errors. Individual data packets including multiple-bit errors may then, for instance, be discarded, and it is only the subsequent data packet corresponding to the subsequent measurement which will be evaluated provided that no multiple-bit error is included therein.

To save power it is, furthermore, particularly advantageous if the processor and control module ($\mu$C) alternately switches on and off the transmitter unit. Thus, the unattended time may, for instance, be 3 to 3.5 s, while the on- or transmission time may, for instance, be 0.6 s. With great changes in the measuring quantities, it is also possible to provide shorter, in particular, variable on/off switching cycles (for instance, with a pulse duty factor of 2:1 instead of about 5:1 to 6:1 as indicated above). In this manner, the transmitter unit requires power supply only for a fraction of time, which is particularly favorable in respect of this circuit component having a rather high power consumption.

It is also advantageous if an internal temperature probe is arranged in the region of the measuring electronics for monitoring the temperature prevailing in the interior of the Dewar vessels. With such a configuration providing control of the internal temperature, it is not only possible to intervene immediately at too high an internal temperature with a view to protecting the electronics, but also to carry out a temperature-dependent measured value correction at the measured data transmitted, if necessary.

For a simplified circuit and in order to do with as little space within the Dewar vessels of the thermally insulated container as possible, it is, furthermore, particularly suitable in case of several measuring probes, if a multiplexer unit is associated with these measuring probes for a multiplex operation of the same.

In order to be able to take into account temperature-dependent variations in analog measuring signal amplification in as simple a manner as possible without having to design particularly complex the measuring electronics contained in the thermally insulated container, it is, furthermore, favorable if the measuring electronics comprises a monitoring circuit for DC parameters, such as, in particular, gain and offset, of an input-side analog measuring signal amplifier of the measuring electronics; the monitoring signals delivered by the monitoring circuit and related to such DC parameters are applied to the processor and control module ($\mu$C) after digitalization in the analog/digital converter and are transmitted to the receiver. In doing so, a particularly simple solution efficient in terms of circuitry may be obtained if the monitoring circuit is designed to comprise a measuring circuit including reference resistors, wherein the respective voltage drop is measured at the measuring resistors in operation to determine gain and offset.

Basically, the most diverse modulation techniques known, such as, in particular, PCM, etc., may be used to transmit the measured data. In order to be able to configure the circuit as small as possible in view of the small space available, it is, however, particularly advantageous if the processor and control module ($\mu$C) is connected to a frequency shift circuit forming an input component of the transmitter unit, which causes e shift in the transmission frequency of the transmission unit at the application of data pulses by the processors and control module ($\mu$C).

In particular, in a rotating autoclave, in which an autoclave rotor is rotatably mounted in an autoclave stator by means of rollers, the radio-transmitted signals containing the measured data, in principle, are disturbed relatively strongly, which is due not only to the vapor atmosphere in the interior of the autoclave, but also to the shielding effect of the autoclave rotor, which is particularly disturbing if, for instance, the transmitting antenna is on the side facing away from an approximately rod-shaped receiving antenna. In order to avoid this and to ensure a safe radio signal transmission and a noisefree radio signal reception, it has proved suitable if the receiving antenna is formed by a frame antenna to be attached to an external autoclave wall along the internal surface and constituting a closed generally circular loop. Such a frame antenna having the form of a circular loop may be a so-called cubical quad antenna, which is electrically connected with the autoclave stator on two diametrically opposite sites and from which the RF signal is extracted at a distance from a connection point to the stator, e.g., of about 60 cm. The effective length of the frame antenna depends on the radio frequency used, wherein a length of about 11 m—which corresponds to the approximate internal dimensions of a conventional autoclave stator—results at a transmission frequency of about 27 MHz.

Moreover, it is advantageous if a digitalization module as well as a processor system, if desired together with a decoder corresponding to the coder of the processor and control module ($\mu$C) of the measuring electronics placed within the thermally insulated container, are provided in the receiver unit to gain the current measured data, such as probe temperatures, from the radio-transmitted signals. In the instant case, the processor system also can effect a correction of the measured data taking into account possible fluctuations of the DC parameters of the analog amplifier of the measuring electronics within the measuring bottle. This measured data correction can be realized by simply multiplying of the measured values transmitted, e.g., in terms of temperature, by the gain value based on a reference value and by a shift in accordance with the offset value, i.e., it holds, for instance:

$$T_{(actual)} = [T_{(measured)} \cdot gain/reference] + offset$$

For an on-line monitoring of the sterilizing process including immediate accessibility, for instance, if the sterilizing temperature decreases by a predetermined level, it is, furthermore, favorable to connect an external computer, e.g., a personal computer (PC), to the processor system of the receiver to transmit the measured data to the same, if desired upon correction of the measured value as indicated above, for on-line evaluation. In this context, a characteristic curve calibration advantageously may be effected in the computer for each measuring subrange, based on the previous calibrations of the measuring probes.

BRIEF DESCRIPTION OF THE DRAWINGS

In the following, the invention will be explained in more detail by way of particularly preferred embodiments illustrated in the drawings, to which it is, however, not limited. In the drawings.

DESCRIPTION OF THE PREFERRED EMBODIMENTS

Figure 2:
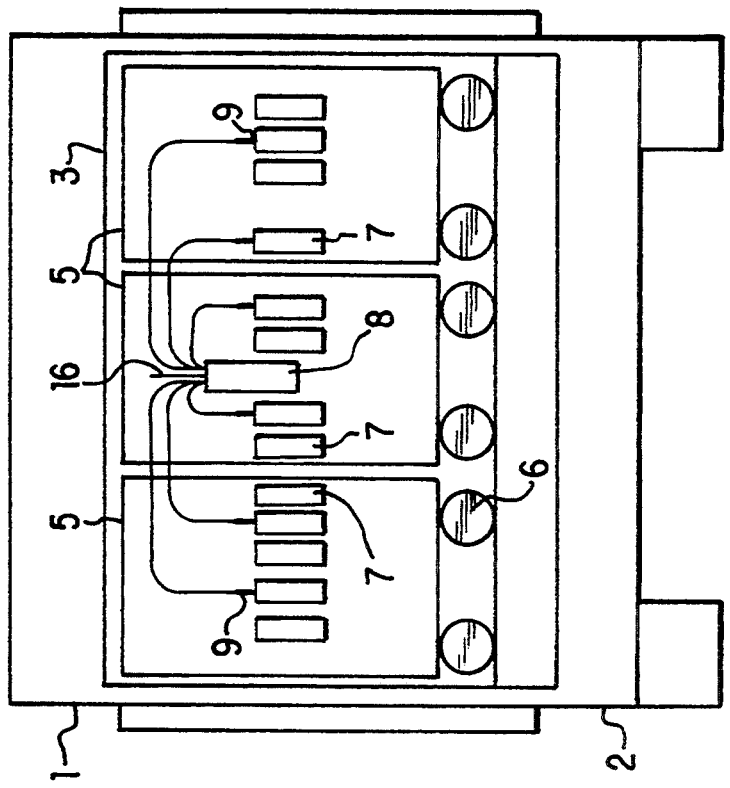
FIG. 2 is a schematic axially sectioned illustration of such a rotating autoclave.
Figure 1:
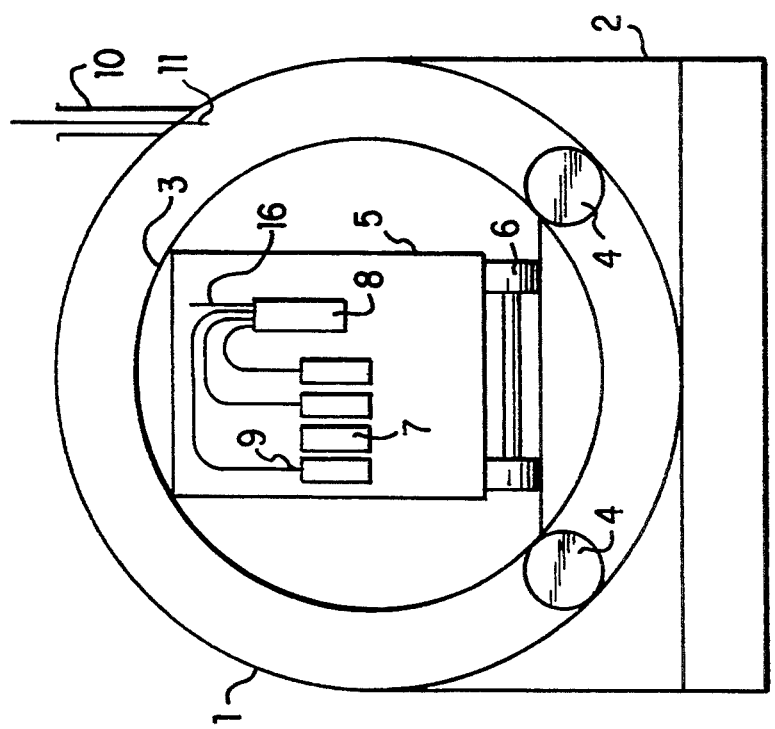
FIG. 1 is a schematic cross sectional illustration of a rotating sterilizer autoclave comprising the temperature measuring arrangement according to the invention.

FIGS. 1 and 2 depict a conventional autoclave generally denoted by 1, in which the present measuring arrangement can be employed in a particularly advantageous manner. It comprises a fixed part, the autoclave stator 2, and a rotating part, the autoclave rotor 3. The autoclave rotor 3 is rotatably mounted in the autoclave stator 2 via rollers 4 (cf. FIG. 1); these rollers 4 are arranged in several pairs distributed over the axial length of the autoclave rotor 3, supporting the cage-like autoclave rotor 3 via bearing races not illustrated as is known per se and need not be explained in detail. At least one of the rollers 4 is set in rotation to rotate the autoclave rotor 3.

In the sterilization treatment to be carried out, separate charging cars 5 are introduced into the autoclave rotor 3 in the axial direction, to which end these cars are equipped with suitable track rollers 6 visible in FIG. 2. The charging cars 5 contain the products to be sterilized, e.g., glass flasks 7 filled with pharmaceutical products.

According to FIGS. 1 and 2, the measuring arrangement which is associated with this autoclave 1 and which, at present, is considered as the most preferred embodiment, comprises a measurement transmitter including a thermally insulated container, which is called measuring bottle 8, and is connected with measuring probes 9, for instance, temperature probes. In FIGS. 1 and 2, the measuring bottle 8 and the measuring probes 9 are associated with various charging cars 5 of the rotating autoclave 1 and the glass flasks 7 placed therein.

In FIG. 1, a receiving antenna 11 is only schematically illustrated, which is attached to the autoclave stator 2 via a leadthrough 10 and is associated with a receiver unit to be explained in more detail later on with reference to FIG. 14, a particularly preferred embodiment of the receiving antenna being discussed in more detail by way of FIG. 13.

Figure 3:
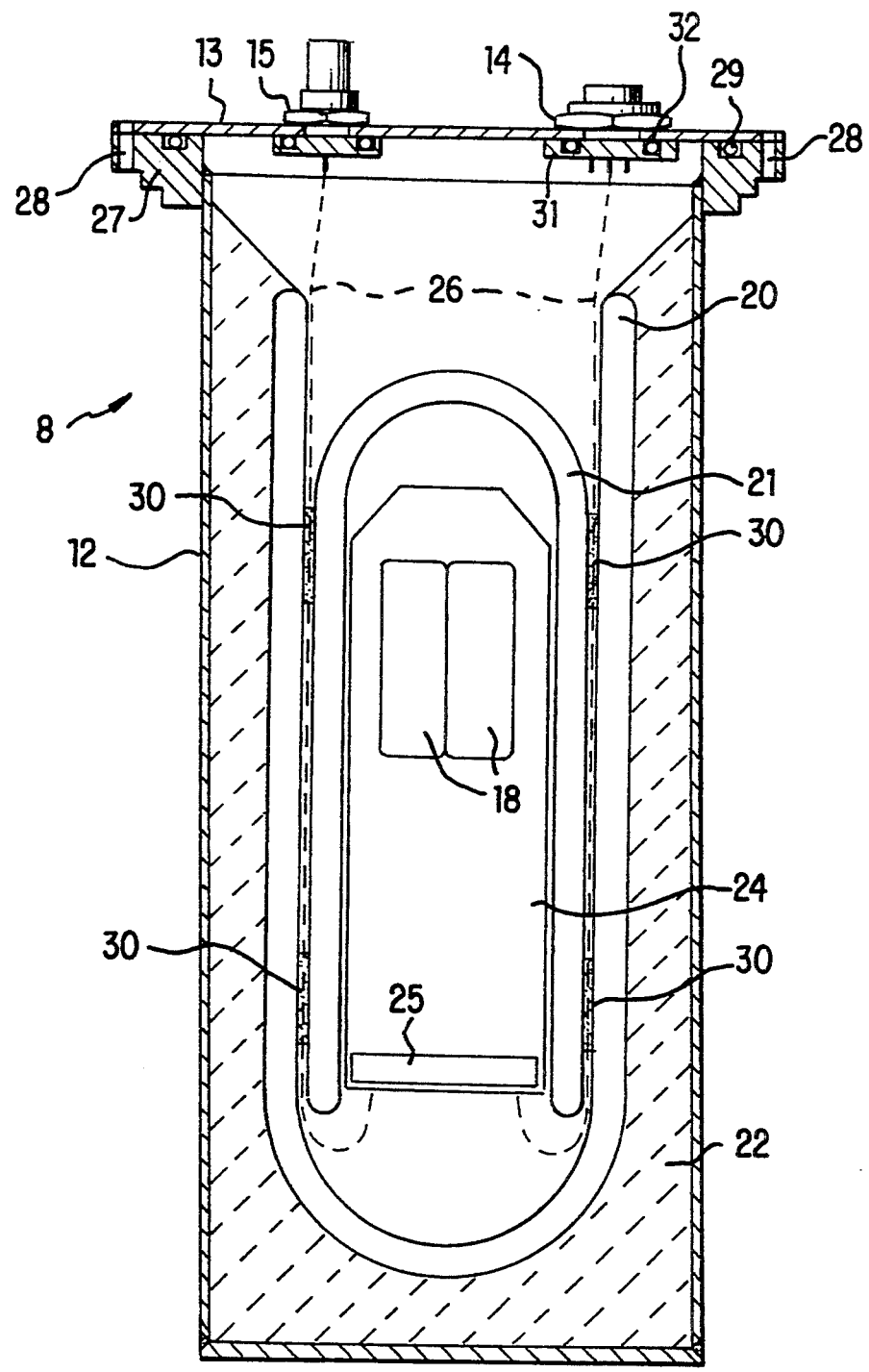
FIG. 3 is an axially sectioned illustration of a so-called measuring bottle (thermally insulated container) of the measuring arrangement according to the invention, to be placed in such a rotating autoclave.
Figure 5:
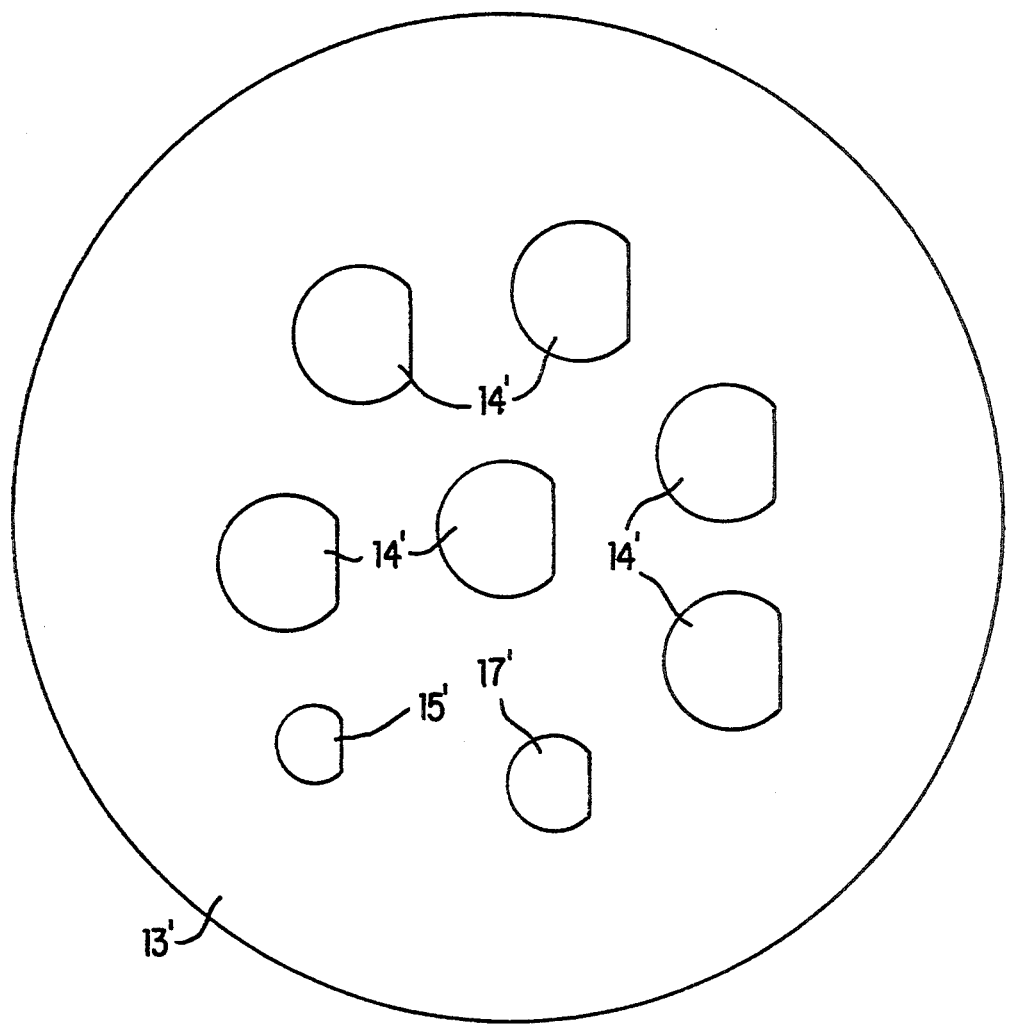
FIG. 5 is a top view onto the lid of the measuring bottle, illustrating the holes for the plug connection elements to be tightly attached.
Figure 4:
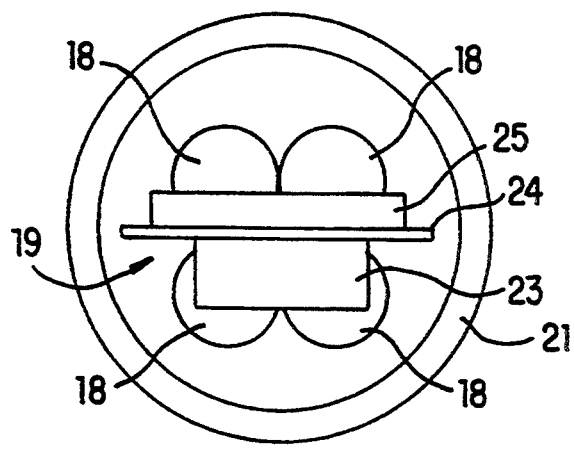
FIG. 4 is a schematic end view of the internal Dewar vessel (from its opened side) with the measuring electronic components contained therein, including four rechargeable batteries (accumulators)

In FIGS. 3 to 5, the measuring bottle 8 is illustrated in detail. This measuring bottle 8 essentially consists of a stainless steel bottle constituting a steel jacket 12 and comprising a lid 13 having, e.g., six (cf. FIG. 5) hermetically sealed plug connection elements 14 for a total of six temperature measuring probes 9, a plug connection element 15 having a longer RF jacket for a transmitting antenna 16 (cf. FIGS. 1, 2, 9 and 12) and a plug connection element 17 for a charging and connecting plug provided for rechargeable batteries contained within the measuring bottle 8 and for their connection to a measuring electronics 19 contained in the measuring bottle 8. It should be noted that in FIG. 5 only the holes for the respective plug connection elements are shown, which, for instance, are cut into the lid 13 made of steel by means of a laser beam. The holes corresponding to the respective plug connection elements 14, 15 and 17 are denoted by the corresponding reference numerals bearing an apostrophe, i.e., 14', 15' and 17', respectively. In contrast to FIG. 3, FIG. 5 also shows a central hole 14' for a central plug connection element 14.

The total of four batteries 18, which are also apparent from FIG. 4 with regard to their number and arrangement, serve to supply the measuring electronics 19 with energy, and the unit comprised of four batteries 18 and of the electronics 19 is placed in the interior of two Dewar glass vessels 20, 21 tightly (e.g., at a distance of 0.5 mm) fitting one into the other, the inner vessel 21 being oriented with its opening downwards and the outer vessel 20 being oriented with its opening upwards. A filling 22 of aluoxide ceramics serves as an additional thermal insulation means. Besides, the measuring bottle 8 is evacuated as well as possible.

As is, furthermore, apparent from FIGS. 3 and 4, the measuring electronics 19, inclusive of a transmitter unit 23, is attached to a printed circuit board 24 also carrying a multipolar plug 25 for the various connection lines 26 to the plug connection elements 14, 15 and 17 provided on the lid 13.

From FIG. 3 it is apparent that the lid 13 of the measuring bottle 8 is screwed on by an annular flange 27 welded on top of the steel jacket 12, as is schematically indicated at 28, an O-ring 29 being additionally interposed to provide a tight closure. It should be noted that the bolt holes for the screw connections 28, which are distributedly arranged over the circumference of the lid 13, have been omitted in the schematic top view of FIG. 5 for reasons of clarity.

Furthermore, it is schematically illustrated at 30 in FIG. 3 that the two Dewar vessels 20, 21 are fastened to each other by means of distributedly arranged adhesive layers, with a uniform distance between the two Dewar vessels 20 and 21 being fixed to be, for instance, 0.5 mm as indicated above. In this narrow intermediate space between the two Dewar vessels 20, 21 there are laid the connection lines 26 leading from the connector 25 on the printed board 24 to the plug connection elements 14, 15 and 17, wherein a relatively long path is provided for these connection lines 26 by the arrangement presented, which surprisingly suffices to prevent the formation of thermal bridges from the lid 13 and the plug connection elements 14, 15, 17 attached thereto, to the measuring electronics 19 provided within the Dewar vessel 21. Moreover, the transmission of heat from the surroundings of the measuring bottle 8 to the measuring electronics 19 is impeded also by the vacuum provided within the measuring bottle 8. However, it is primarily the two Dewar vessels 20, 21 that provide for a substantial insulating effect.

Figure 6:
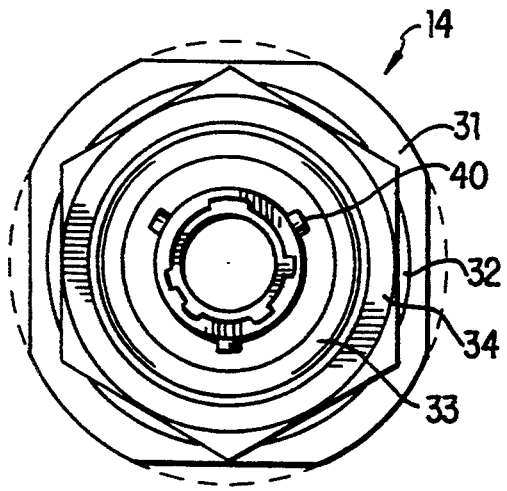
FIGS. 6 and 7 are a top view and an elevational view, respectively, of a plug connection element (jack element) to be attached to the lid of the measuring bottle.
Figure 7:
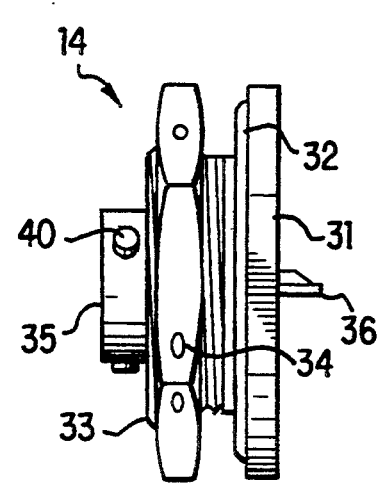

For the sake of completeness, plug connection elements of a conventional design are illustrated in FIGS. 6 and 7 in top view and in side view, which plug connection elements, for instance, are those serving to connect the connection lines which are associated with the measuring probes 2 and previously denoted by 14. It should be mentioned that the plug connection elements 15 and 17 for the transmitting antenna 16 and for recharging the batteries 18 as well as connecting the measuring electronics 19 to the batteries 18, respectively, may be designed in a similar manner having slightly differing dimensions.

The plug connection elements attached to the lid 13, e.g., 14, in a conventional manner comprise a lower stop plate 31 including an O-ring 32 that comes to lie at the lower side of the lid 13 in the mounted state (cf. also FIG. 3). A fastening ring 34 is screwed on a threaded socket 33 molded with the lower stop plate 31. A connection jack 35 serves as the electric connection component proper, containing, for instance, one (or several) contact(s) (not illustrated) electrically communicating with one (or several) terminal lug(s) 36 on the lower side of the plug connection element 14 and cooperating with a corresponding complementary electric connector part 37 (cf. FIG. 8) which is connected with the connection line leading to the respective measuring probe 9, or which is attached to the transmitter antenna 16 (cf. FIG. 12), to a connection cable not illustrated to be used for recharching the batteries or to a connection component destined to connect the measuring electronics 19 to the batteries 18.

By means of a plug connection element 14 (or 15 or 17) tightly fastened to the lid 13 as described above, it is, for instance, possible to limit the penetration of air into the interior of the evacuated measuring bottle 8 to a value of $1 \times 10^{-7}$ cm$^3$ per second.

Figure 8:
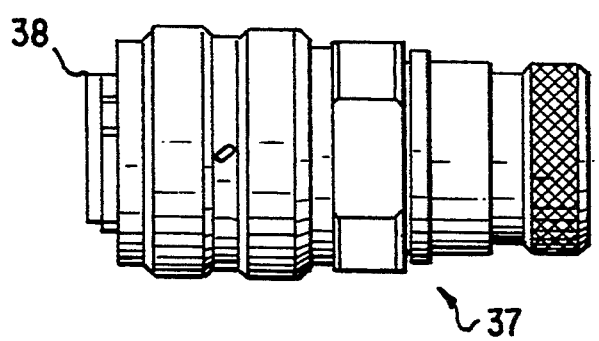
FIG. 8 is a view of a complementary plug connection element or connector cooperating with a plug connection element (jack element) according to FIGS. 6 and 7.

In FIG. 8, a likewisely conventional-design connector part 37 is represented, which connector part, for instance, is designed to connect the connection lines for the measuring probes 9 via a conventional shrink adapter (not illustrated) to be slipped onto the right side of the connector part 37. On the left-hand side of FIG. 8, the connector part 37 comprises a coupling part 38 that is complementary to the jack element 35 of the plug connection element 14 according to FIGS. 6 and 7, wherein a bayonet connection including slits not indicated in FIG. 8 (yet, cf. FIG. 12, in which such a slit is schematically indicated at 39 on a comparable RF-connector part 37') is provided in a conventional manner, into which the radial pins 40 apparent from FIGS. 6 and 7 are inserted.

Such couplings or plug connections as described above by way of FIGS. 6 to 8 are known per se and need not be further explained.

Figure 9:
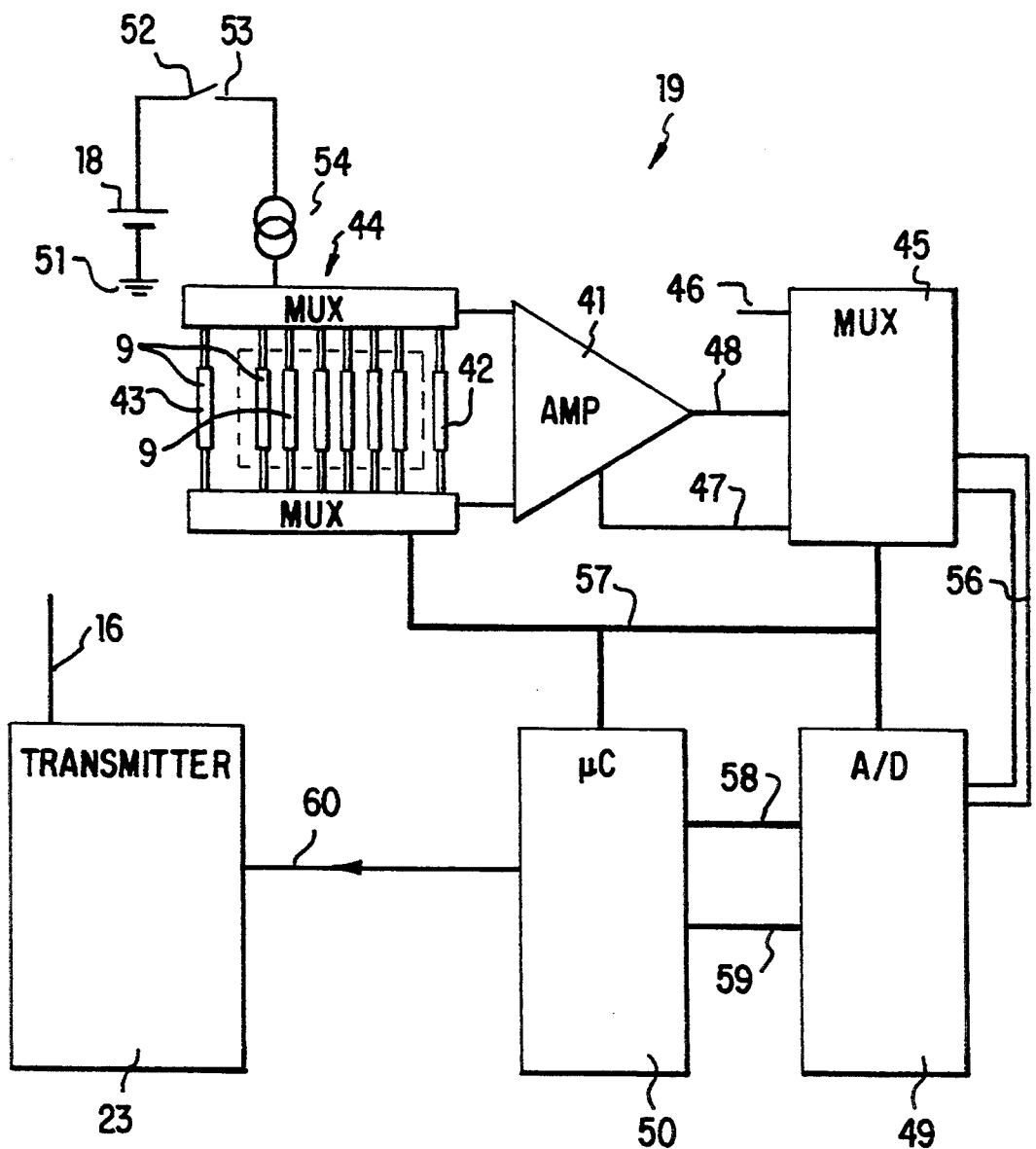
FIG. 9 is a block diagram of the measuring electronics of the measuring set-up contained in the measuring bottle.

According to FIG. 9, the measuring bottle electronics 15, in general, comprises an analog measuring signal precision amplifier 41, which is connected with the measuring probes 9—e.g., Pt 100 temperature measuring resistors—as well as—in the instant example—with an internal temperature probe 42 arranged within a measuring bottle 8, such as an internal temperature measuring resistor. Furthermore, it is connected to a reference measuring resistor 43. A multiplexer unit 44 is associated to the group consisting of measuring resistors and probes 9, 42 and 43, and a multiplexer monitoring circuit 45 is provided for measuring the battery voltage (terminal 46) as well as, in particular, for monitoring DC parameters of the amplifier 41, i.e., offset and gain (line 47), and for receiving and further transmitting the measuring signals proper, which are derived from the measuring probes 2, 42 (line 48), in multiplex operation, to an A/D converter 49. Then, a control and processor module in the form of a microcontroller ($\mu$C) 50 and a transmitter unit (RF.component) 23 including the transmitting antenna 16 connected thereto are provided. The multiplexer unit 44 is provided for switching the measuring probes and resistors 9, 42, 43, and an appropriate multiplex operation is provided also for the monitoring circuit 45. A watchdog (not illustrated) may be associated to the monitoring circuit 45 as a protection means against program failures. Such a watchdog is known per se and need not be explained herein.

As already mentioned, four rechargeable batteries 18 serve to supply the measuring electronics 19 with energy, for instance, four NiCd accumulators with 500 mAh. These batteries 18 are schematically indicated in FIG. 9, their terminals 51 and 52 as well as terminal 53 leading to the electronics 19 proper being led to the above-mentioned plug connection element 17 in order to be able to recharge the accumulators 18 via the terminals 51, 52 or to connect the terminals 52 and 53 with each other via a connecting bridge provided on the complementary connector part to be slipped on, thus switching the measuring electronics 19 on the voltage source.

In order to provide for a largely constant power supply, a conventional-design constant current source 54 is additionally associated to the measuring electronics 19, which is only symbolically represented in FIG. 9. This constant current source 54 delivers a constant current of, for instance, 1.298 mA, to flow into the respective temperature measuring resistor 9 or 42 or into the reference resistor 43, depending on the position of the multiplexer unit 44.

Figure 10:
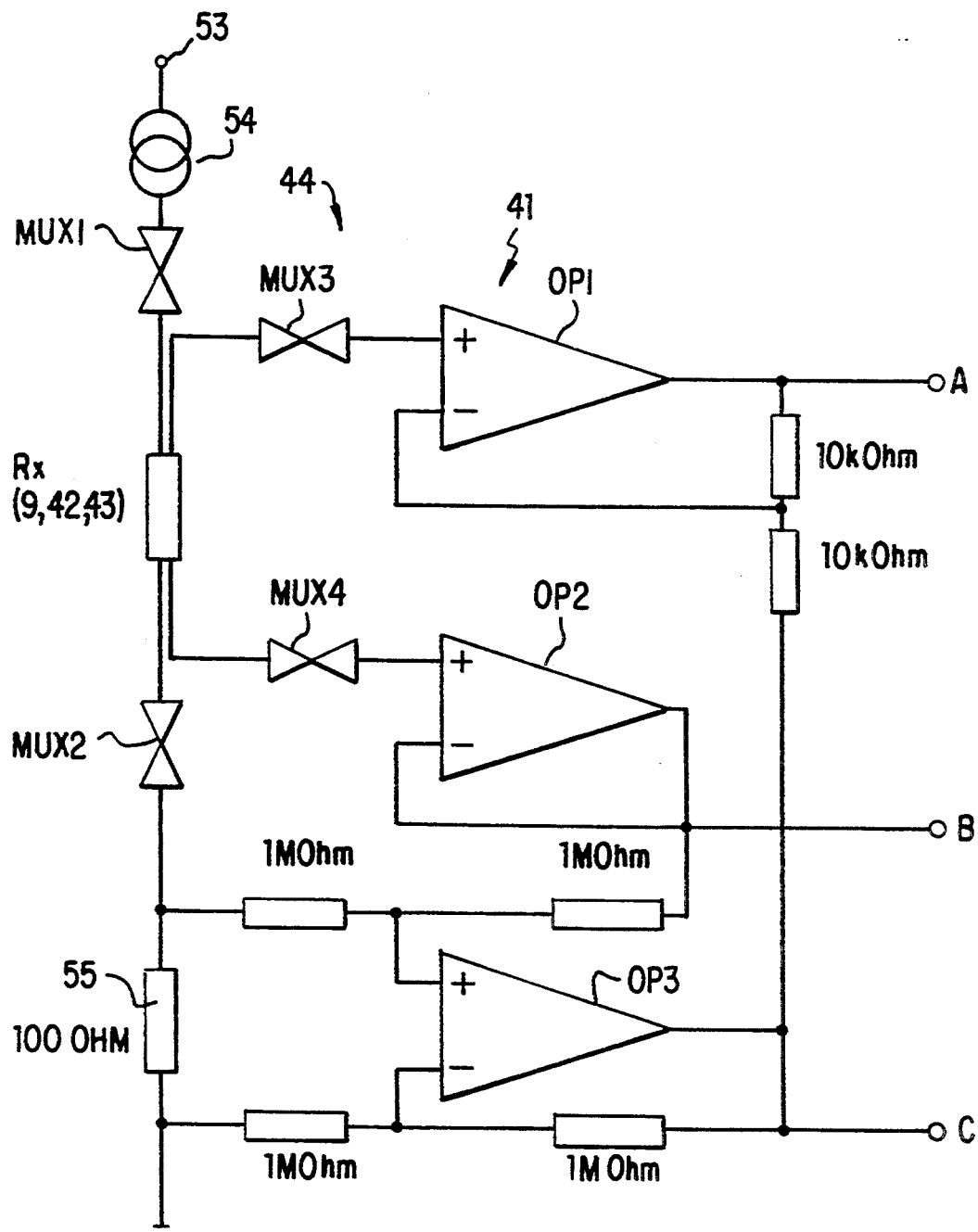
FIG. 10 is a detailed block diagram of an analog measuring signal amplifier and a multiplexer unit of this measuring electronics according to FIG. 9.

As is more clearly apparent from FIG. 10, the multiplexer unit 44 comprises four individual multiplexers MUX1, MUX2, MUX3 and MUX4. The multiplexers MUX1 and MUX2 are responsible for measuring the power flow at each measuring resistor 9, 42 and 43, respectively, symbolically indicated by $R_X$ in FIG. 10 (this being one of the eight measuring and reference resistors each as indicated) and the multiplexers MUX3 and MUX4 are responsible for voltage measurement. These multiplexers MUX1 to MUX4, for instance, are comprised of conventional multiplexer components of the type 4051, while the multiplexer monitoring circuit 45, for instance, is a 4052 type circuit.

The analog measuring signal amplifier generally depicted in FIG. 9 and denoted by 41, according to FIG. 10 incorporates three operational amplifiers OP1, OP2 and OP3, wherein the circuit represented in FIG. 10 at the same time comprises a measuring circuit for controlling the DC parameters gain and offset of the amplifier circuit 41. In this context, a further reference precision resistor 55 having a value of, e.g., 100 Ω, is provided such that a voltage drop of 129.8 mV is caused at this resistor 55 if the power of the constant power source 54 amounts to 1.298 mA as indicated. Accordingly, the voltage $U_{BC}$ between the two output terminals B and C normally amounts to 129.8 mV, the voltage between the output terminals B and C ($U_{BC}$), in general, being a measure for the respective gain value of the amplifier circuit 41, i.e., the reference resistor 55 serves to detect possible gain changes. This determination takes place irrespective of which measuring resistor $R_X$ (2, 42 or 43) has been connected to the circuit via the multiplexers MUX1 to MUX4 at that moment.

On the other hand, the above-mentioned reference resistor 43 (cf. FIG. 9) serves to determine the offset value of the analog amplifier circuit 41. Again, this reference resistor 43, for instance, is a precision resistor having a value of 100 Ω. The respective offset value is then taken from the voltage $U_{AC}$ applied between the output terminals A and C; this voltage $U_{AC}$ is calculated from the voltage drop at the reference resistor 43 (in the preceding example at a resistance value of 100 Ω, hence 129.8 mV), from which voltage drop the voltage at the gain measuring resistor 55 is deducted by aid of the operational amplifier OP3. In the ideal case, this yields a value of 0 V. However, if the resistance value of the reference resistor 43 has changed, e.g., on grounds of temperature increases, a certain value results for this difference, which is doubled by the amplifier circuit including the operational amplifier OP1 (forming a double non-inverting operational amplifier, whereas OP2 is a voltage follower). Thus, it holds:

$$U_{AC} = 2 \cdot (R_x \cdot 1.298 \text{ mA} - 129.8 \text{ mV})$$

For instance, the resistance value of the measuring resistor 9 (FIG. 9) at a product temperature (bottle temperature) of 100° C. increases from 100 Ω to 138.5 Ω, and, accordingly, a value of 99.24 mV results for $U_{AC}$.

As pointed out above, the amplification of the arrangement is, in turn, constantly controlled and measured, the gain value (amplification) in this case ideally being 129.8.

As indicated, the values for these DC parameters offset and gain are applied to the multiplexer monitoring circuit 45 via connection line 47 schematically illustrated in FIG. 9 and from there are fed to the A/D converter 49 via signal lines 56 for digitalization.

The amplification and measuring circuit 41, 45 described, thus, yields a practically linear relation between the respective temperature and the output voltage of the measuring circuit. The circuit does without adjusting controller, using only precision resistors with a tolerance of, e.g., 0.02% at 5 ppm° C. in the measuring component. The circuit components, moreover, also are designed such that the respective signal intensity (in mV) already corresponds to the respective measured value (in °C.).

Subsequently, the values for offset and gain, together with the temperature values measured, are radio-transmitted to the receiver unit (FIG. 14), where a measured value correction is effected, which will be explained in more detail later on with reference to FIG. 15.

For the sake of completeness, a control bus 57 as well as—between the A/D converter 49 and the microcontroller 50—a data bus 58 and an address bus 59 are represented, these bus lines being provided in a conventional manner. In addition, it should be mentioned that, for instance, the module Maxim 7109 may be used as the A/D converter 49 and the module 87C51 may be used as the microcontroller 50.

The microcontroller 50 controls the various multiplexers and the A/D converter 49 via the control bus 57; through line 60, it delivers data to the transmitter unit 23 on the basis of the data received via the data bus 58, in accordance with the measured values of the six measuring probes 9 and of the internal measuring probe 42 as well as in accordance with the offset value and the gain value and, furthermore, in accordance with the accumulator voltage value (in %) monitored by the monitoring circuit 45 via line 46. The microcontroller 50 alternately switches on and off the transmitter unit 23. Switching on and off may be effected at shorter or longer time intervals depending on the changes in the measuring signals. When a relatively stable temperature situation has been reached, the transmitter unit 23 may be activated, for instance, every 3.5 s for a transmission time of 0.6 s to send a data packet via the transmitting antenna 16.

The data are Hamming-coded by the microcontroller 50 such that an error correction or error recognition will be possible. By Hamming codation, the correction of 1-bit errors is rendered feasible during transmission and the detection of multi-bit errors is permitted.

The transmitter unit 23 may be constituted by a conventional RF transmitter circuit including conventional oscillating and filtering circuits. Data transmission may be realized by simple frequency modulation, i.e., in particular, by a simple frequency shift of the transmission frequency (modulation type F1).

Figure 11:
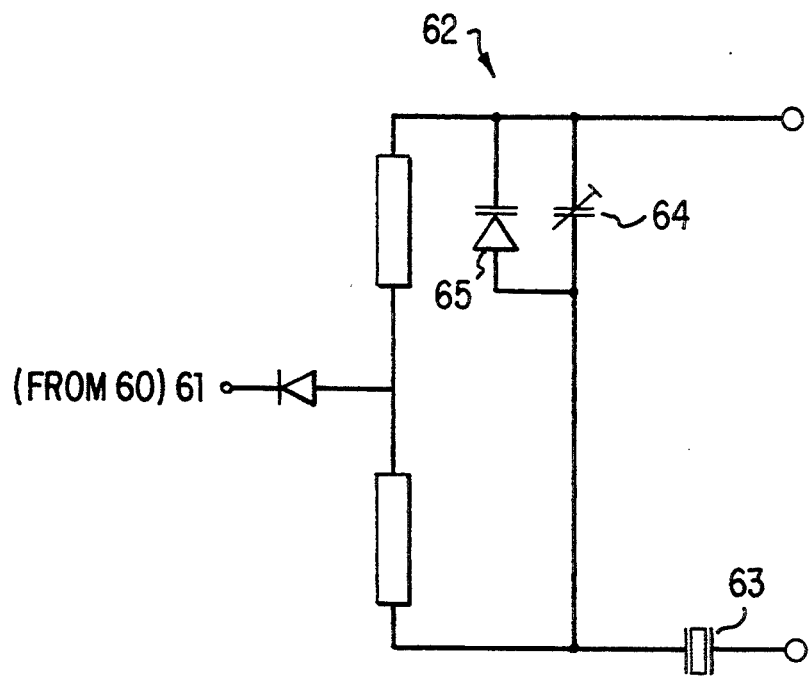
FIG. 11 is a detailed block diagram of a frequency shift circuit of the transmitter unit of the measuring electronics according to FIG. 9.

In FIG. 11, a part of the transmitter unit 23 is shown, i.e., that part which is responsible for the frequency shift. The consecutively arranged circuits, such as oscillator, filter, etc., are of conventional design and need not be explained.

In detail, the low frequency pulses (data pulses) are applied to the terminal 61 of the frequency shift circuit 62 via line 60. This frequency shift circuit incorporates a tuning capacitor (trimmer) 64 as well as a varicap diode (variable capacitance diode) 65 in addition to a RF-frequency-determining quartz 63. By this trimmer 64, which, for instance, covers a range of from 2 to 10 pF, the carrier frequency of the transmitter unit 23, is tuned to, e.g., 27.255 MHz, precisely to ±10 Hz. If low frequency pulses are applied, the capacity diode 65 causes a shift in the carrier frequency, the frequency variation, for instance, being ±1.5 kHz.

Figure 12:
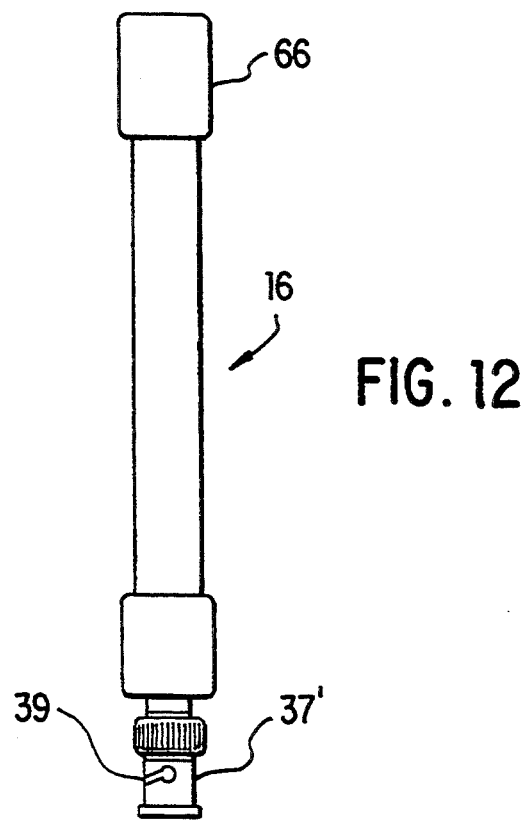
FIG. 12 is an illustration of a transmitting antenna associated to this transmitter unit, including a plug connection element.

The RF signal is radiated via the transmitting antenna 16, which may be a quarter-wave radiator having an effective length of 105 cm. The antenna wire may be a wire of stainless steel having a diameter of 1.5 mm, which wire is wound to a helix having a diameter of 15 mm and a length of about 150 mm. On this helix a heat-shrinkable sleeve is shrunk, which is made of a conventional synthetic material, such that an overall rod-shaped configuration will be obtained as indicated in FIG. 12, which rod is closed by a cap 66 on its end located opposite the connector part 37'. The transmitting antenna 16 also may be designed as a quarter-wave radiator having an extended length of 100 cm. Thereby, the radiation properties will be improved.

Figure 13:
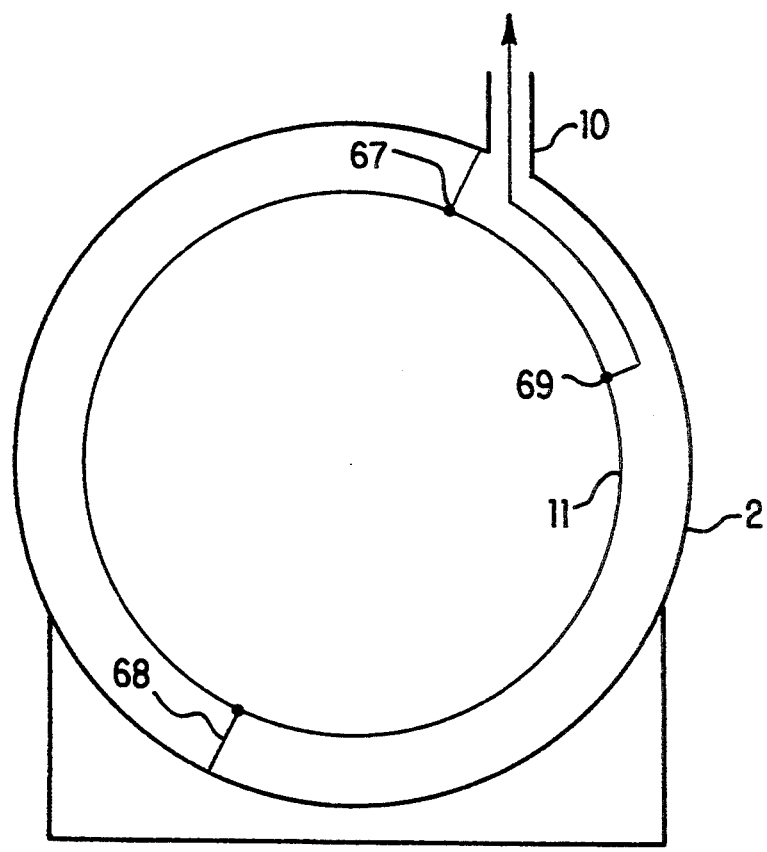
FIG. 13 is a front view of a frame antenna used as a receiving antenna, with the wall of the autoclave stator being schematically illustrated as well.

In FIG. 13, the pertaining receiving antenna 11 is illustrated, which is a frame antenna (cubical quad antenna) placed in the interior of the autoclave stator 2 as a circular loop. In detail, the receiving antenna 11 is comprised of a stainless steel round wire having a thickness of, for instance, 2 mm, which is mounted to the internal wall of the stator casing of the autoclave stator 2 at a distance of about 5 cm by means of spacers (not illustrated). The receiving antenna 11, furthermore, is electrically connected with the internal wall of the autoclave at two diametrically opposite points 67, 68, the RF output signal being extracted at a point 69 spaced apart from the one wall connection point 67, for instance, by 60 cm and being conducted to the receiver unit proper (cf. FIG. 14) via a coaxial line through the leadthrough 10. The effective length of the frame antenna 11 in this case is about 11 m, which corresponds to the circumferential length of conventional vessel walls of rotating autoclaves (diameter approx. 2.5 m), hence also the RF transmission frequency of about 27 MHz as indicated above. As proved by experiments, a receiving antenna 11 in the form of a frame antenna as described always guarantees the noise-free reception of the RF signals delivered from the transmission unit 23 through the antenna 16, even with the autoclave rotor 3 rotating, despite the difficult conditions prevailing, such as water vapor, shielding by the rotor cage, etc.

Figure 14:
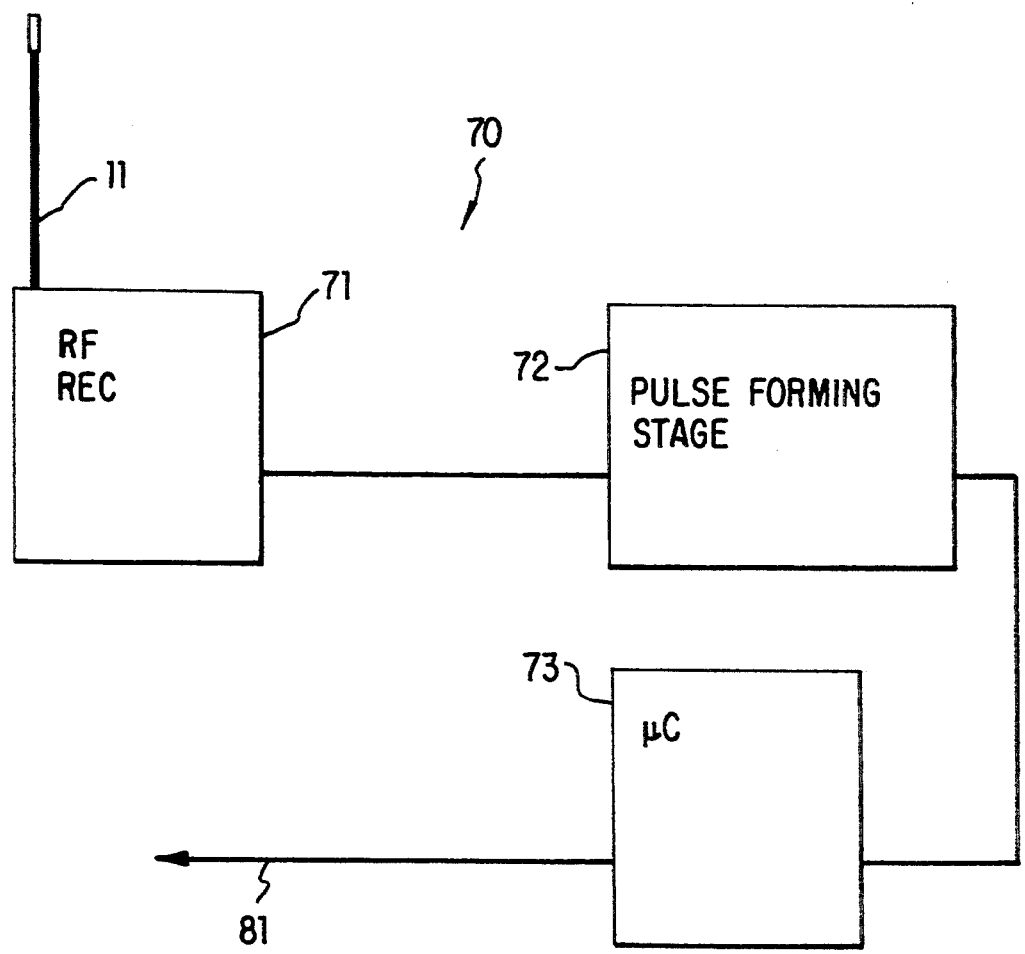
FIG. 14 is a block diagram of the external receiver unit.

FIG. 14 is a block diagram of the entire receiver unit 70 including the receiving antenna 11. The receiver unit 70 comprises a RF receiver circuit 71, which may, for instance, be a completely conventional heterodyne receiver. The demodulated RF output signal of this receiver circuit 71 then is supplied to a pulse forming circuit 72, and the thus regained digital data signal is fed to a microcontroller system 73. The microcontroller incorporated in this microcontroller system 73 together with other modules, such as the main memory (RAM) and the program memory (EPROM) in a manner known per se decodes the digital signal fed (Hamming code), carrying out a plausibility check. In this context, it is also referred to the flow chart according to FIG. 15, in which the program sequence of the microcontroller system 73 is represented.

Figure 15:
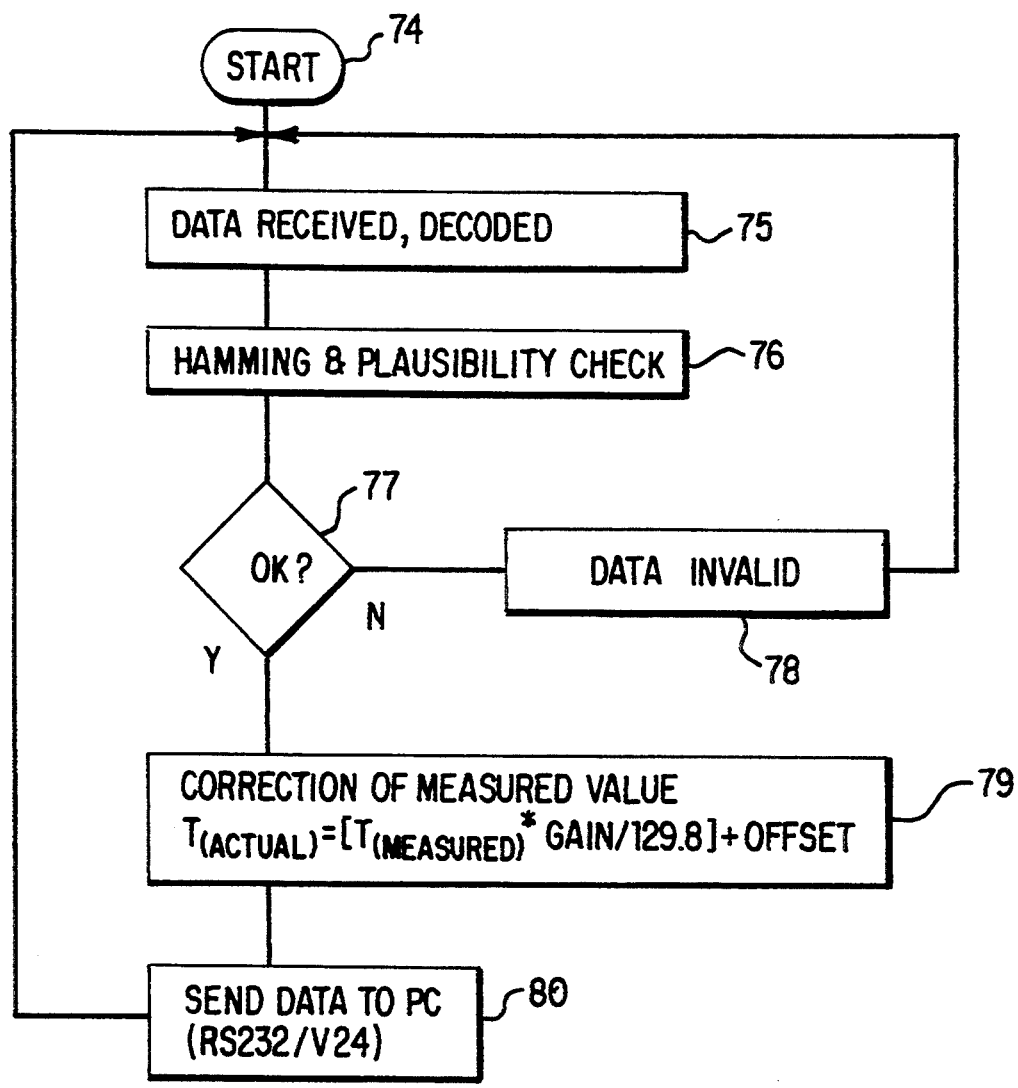
FIG. 15 is a flow chart illustrating the measured data correction carried out in the receiver unit at changing offset and gain values of the analog measuring signal amplifier of the measuring electronics according to FIGS. 9 and 10.

In detail, according to FIG. 15, the respective data package is received and decoded in a step 75 after a starting step at 74. In a subsequent step 76, the Hamming decodation and the plausibility check are carried out, the pertaining interrogation whether the data packet is acceptable or not taking place at 77. In the plausibility check, it may, for instance, be checked whether the temperature change from one measuring cycle to the other is smaller than ±5° C., an error measurement being taken for granted at greater changes. If the result of the interrogation at 77 is negative, the data are taken for invalid according to block 78, and it is returned to block 75 to receive and decode the subsequent data packet.

If, however, the result of the check according to block 77 is positive, i.e., the data are recognized as plausible, a measured value correction according to the following relation $$T(\text{actual}) = T(\text{measured}) \cdot \text{gain}/129.8 + \text{offset}$$

is carried out at block 79. Thus, changes in the DC parameters of the analog measuring signal amplifier 41 (cf. FIG. 9) are taken into account in determining the measured values, the gain reference value of 129.8 in the instant example resulting from the above-indicated value for the constant current of the constant current source 54.

In a final step 80, the decoded, checked and corrected data are sent to an external computer, for instance, via an interface RS232/V24, as is also schematically illustrated at 81 in FIG. 14. After this, the program is returned to the start.

The external computer (not illustrated in the drawing), in particular, may be a personal computer (PC), and in this computer further processing of the temperature data, i.e., in particular, a characteristic curve calibration, can be realized; this characteristic curve calibration is effected on the basis of preceding calibrations of the temperature measuring probes 9 carried out in respect of individual subranges of the total measuring range in order to attain a high overall measuring accuracy. As proved by experiments, a measuring accuracy of ±0.15° C. can be attained over the total measuring range (e.g., from 0° to 150° C.). Thereby, an extremely precise process control is possible in the sterilization of pharmaceutical products, which is of a particular relevance because there predetermined temperatures must be observed over predetermined period of times with great accuracy. For instance, the sterilization temperature to be observed at a sterilization with water vapor is 121° C. at a sterilization time of 20 min. Already relatively slight temperature deviations could render a repeated sterilization treatment necessary, yet on-line control is possible in the instant case such that it can be intervened immediately at beginning changes of the sterilization temperature by readjusting this temperature to the desired value. Hence, relatively short, yet reliable sterilization treatments are ensured, on the whole, such that the arrangement according to the invention yields considerable time and costs savings.

Although the invention has been explained in detail by way of particularly preferred embodiments, changes and modifications are possible within the scope of the invention. Thus, known sensor modules, such as semiconductor probes, may, for instance, be used as measuring probes instead of the temperature measuring resistors (Pt 100). Moreover, inductive energy transmission may be effected for supplying the measuring electronics in the measuring bottle with energy, wherein a coil encloses, e.g., the autoclave rotor and is connected with the measuring electronics within the measuring bottle, a pertaining second coil (primary winding) being mounted in the interior of the autoclave stator.

What we claim is:

1. In a measuring arrangement to be used for autoclaves or similar devices under heavy climatic conditions and of the type including at least one measuring probe, such as a temperature measuring probe, for detecting physical quantities to be measured and delivering resulting measured data, a thermally insulated container having a lid, a measuring electronics arranged in said thermally insulated container, a first connection line leading from said measuring electronics to said lid to connect said measuring electronics with said at least one measuring probe, said measuring electronics including a transmitter unit, a transmitting antenna being arranged outside of said container on said lid and a second connection line being provided to connect said antenna with said transmitter unit, and a separate receiver unit, a receiving antenna being associated to said separate receiver unit, the improvement comprising:
- two oppositely oriented Dewar vessels contained in said thermally insulated container and arranged one within the other, thus constituting an inner Dewar vessel adapted to accommodate said measuring electronics and an outer Dewar vessel providing an interspace relative to said inner Dewar vessel for leading through said first and second connection lines,
- first coupling means tightly provided in said lid of said container and connected with said connection lines led through said interspace,
- corresponding second coupling means associated with said first coupling means and adapted to be connected to said transmitting antenna and to said first connection line, and
- an analog/digital converter for digitalizing said measured data as well as a digital control and processor module, provided in said measuring electronics, said transmitter unit following upon said digital control and processor module.

2. A measuring arrangement as set forth in claim 1, further comprising third coupling element attached to said lid of said thermally insulated container and rechargeable battery means connected to said third coupling means, said measuring electronics having power supply terminals also connected to said third coupling means.

3. A measuring arrangement as set forth in claim 1, characterized in that said first coupling means and said second coupling means are plug connection means.

4. A measuring arrangement as set forth in claim 1, wherein said two Dewar vessels are embedded in an insulation layer of aluminum oxide ceramics.

5. A measuring arrangement as set forth in claim 1, wherein said processor and control module comprises coding means for coding the digitalized measured data.

6. A measuring arrangement as set forth in claim 5, wherein said coding means is a Hamming coder.

7. A measuring arrangement as set forth in claim 1, wherein said processor and control module comprises switching means for alternately switching on and off said transmitter unit.

8. A measuring arrangement as set forth in claim 1, further comprising an internal temperature probe arranged in the region of said measuring electronics and adapted to monitor the temperature prevailing within said Dewar vessels.

9. A measuring arrangement as set forth in claim 1 including a plurality of measuring probes, further comprising a multiplexer unit associated to said measuring probes for multiplex operation of said measuring probes.

10. A measuring arrangement as set forth in claim 1, said measuring electronics further comprising an input-side analog measuring signal amplifier and a DC parameter monitoring circuit, said monitoring circuit delivering monitoring signals related to DC parameters of said measuring electronics and said monitoring signals being applied to said processor and control module after digitalization in said analog/digital converter for transmission.

11. A measuring arrangement as set forth in claim 10, wherein said DC parameters comprise gain and offset of said analog measuring signal amplifier, and wherein said monitoring circuit comprises a measuring circuit including measuring resistor means and reference resistor means for measuring the respective voltage drop at the respective measuring resistor means during operation so as to determine said gain and offset.

12. A measuring arrangement as set forth in claim 1, further comprising a frequency shift circuit connected to said processor and control module and constituting an input component of said transmission unit, said frequency shift circuit causing a shift in the transmission frequency of said transmission unit during application of data pulses by said processor and control module.

13. A measuring arrangement as set forth in claim 1, wherein said receiving antenna is comprised of a frame antenna provided to be attached along the internal surface of an external wall of said autoclave and forming a closed generally circular loop.

14. A measuring arrangement as set forth in claim 1, further comprising a digitalization module and a processor system provided in said receiver unit and adapted to gain current measured data, such as probe temperatures, from radio-transmitted signals.

15. A measuring arrangement as set forth in claim 5, further comprising a digitalization module and a processor system provided in said receiver unit and adapted to gain current measured data, such as probe temperatures, from radio-transmitted signals as well as decoding means provided in said receiver unit, said decoding means corresponding to said coding means of said processor and control module of said measuring electronics provided in said thermally insulated container.

16. A measuring arrangement as set forth in claim 14, further comprising an external computer connected to said processor system to transmit said measured data for on-line evaluation.

17. A measuring arrangement for use under heavy climatic conditions in autoclaves or similar devices, the measuring arrangement comprising:
- a thermally insulated container having a lid;
- at least one measuring probe;
- measuring electronics including a transmitter;
- a first connection line extending through said insulated container and being provided to connect said measuring electronics with said at least one measuring probe;
- a transmitting antenna arranged outside of said container;
- a second connection line extending through said insulated container and being provided to connect said antenna with said transmitter;
- two oppositely oriented Dewar vessels located within said thermally insulated container and arranged one within the other, thus constituting an inner Dewar vessel adapted to accommodate said measuring electronics and an outer Dewar vessel providing an interspace relative to said inner Dewar vessel for leading through said first and second connection lines; and
- a receiver unit having a receive antenna.

* * * * *

UNITED STATES PATENT AND TRADEMARK OFFICE
CERTIFICATE OF CORRECTION

PATENT NO. : 5,426,428
DATED : June 20, 1995
INVENTOR(S) : Hans Binder et al.

It is certified that error appears in the above-indentified patent and that said Letters Patent is hereby corrected as shown below:

On the title page, in item [54], The title should be changed to -- MEASURING ARRANGEMENT FOR AUTOCLAVES --; In the Abstract: Line 18, delete "means"; Col. 6, line 17, "e" should be -- a --; Col. 6, line 19, "processors" should be -- processor --.

Signed and Sealed this

Nineteenth Day of September, 1995

Attest:

BRUCE LEHMAN

Attesting Officer     Commissioner of Patents and Trademarks